(12) United States Patent
Bizup et al.

(10) Patent No.: US 8,021,324 B2
(45) Date of Patent: Sep. 20, 2011

(54) VENOUS ACCESS PORT ASSEMBLY WITH X-RAY DISCERNABLE INDICIA

(75) Inventors: Raymond Bizup, Feasterville, PA (US); Kevin Sanford, Chalfont, PA (US); Christopher Linden, Allentown, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/175,182

(22) Filed: Jul. 17, 2008

(65) Prior Publication Data
US 2009/0024098 A1 Jan. 22, 2009

Related U.S. Application Data

(60) Provisional application No. 60/961,133, filed on Jul. 19, 2007.

(51) Int. Cl.
*A61M 37/00* (2006.01)

(52) U.S. Cl. ............... 604/88; 604/175; 604/288.04

(58) Field of Classification Search ........... 604/288.01–288.04, 86, 88, 116, 604/167.02
See application file for complete search history.

(56) References Cited

U.S. PATENT DOCUMENTS

| | | | |
|---|---|---|---|
| 1,713,267 A | 5/1929 | Crowley | |
| 2,891,689 A | 6/1959 | Gould | |
| D198,453 S | * | 6/1964 | Weichselbaum |
| 3,293,663 A | 12/1966 | Cronin | |
| 3,341,417 A | 9/1967 | Sinaiko | |
| 3,518,428 A | 6/1970 | Ring | |
| 3,829,904 A | 8/1974 | Ling et al. | |
| 3,831,583 A | 8/1974 | Edmunds, Jr. et al. | |
| 3,915,162 A | 10/1975 | Miller | |
| 3,919,724 A | 11/1975 | Sanders et al. | |
| 3,951,147 A | 4/1976 | Tucker et al. | |
| 4,027,391 A | 6/1977 | Samis et al. | |
| 4,121,108 A | 10/1978 | Manor | |

(Continued)

FOREIGN PATENT DOCUMENTS

EP 0619101 A1 10/1994

(Continued)

OTHER PUBLICATIONS

Intl Search Report dated Dec. 1, 2008; PCT/US2008/070330 (5 pages).

(Continued)

*Primary Examiner* — Nicholas D Lucchesi
*Assistant Examiner* — Gerald Landry, II
(74) *Attorney, Agent, or Firm* — Blank Rome LLP (57) ABSTRACT

A venous access port assembly (10) having a housing base (28) with a discharge port (16), a septum (14) and a cap (48), with an interior reservoir (22). The housing base (28) is provided with X-ray discernable indicia (100,200) to identify an attribute of the assembly (10) after its implantation and clearly appear on an X-ray of the patient in a manner informing the radiologist or technologist and the medical practitioner of that particular attribute. Such indicia can be depicted as cutouts (102) through a disc of radiopaque material (100) where the cutouts are in the form of alphabetical letters such as "CT", or can be a set (200) of discrete elements (202) of radiopaque material, that are affixed along the bottom surface of the housing base or embedded within the thickness of the bottom housing wall.

44 Claims, 4 Drawing Sheets

U.S. PATENT DOCUMENTS

| | | | |
|---|---|---|---|
| 4,190,040 A | 2/1980 | Schulte | |
| 4,194,122 A | 3/1980 | Mitchell et al. | |
| 4,202,349 A | 5/1980 | Jones | |
| 4,274,006 A | 6/1981 | Caine | |
| 4,349,498 A | 9/1982 | Ellis et al. | |
| 4,361,153 A | 11/1982 | Slocum et al. | |
| 4,406,567 A | 9/1983 | Samis et al. | |
| 4,445,896 A | 5/1984 | Gianturco | |
| 4,450,592 A | 5/1984 | Niederer et al. | |
| 4,456,011 A | 6/1984 | Warnecke et al. | |
| 4,469,483 A | 9/1984 | Becker et al. | |
| 4,494,545 A | 1/1985 | Slocum et al. | |
| 4,543,088 A | 9/1985 | Bootman et al. | |
| 4,549,879 A | 10/1985 | Groshong et al. | |
| 4,559,046 A | 12/1985 | Groshong et al. | |
| 4,576,595 A | 3/1986 | Aas et al. | |
| 4,627,844 A | 12/1986 | Schmitt | |
| 4,634,427 A | 1/1987 | Hannula et al. | |
| 4,636,213 A | 1/1987 | Pakiam | |
| 4,653,508 A | 3/1987 | Cosman | |
| 4,655,765 A | 4/1987 | Swift | |
| 4,662,652 A | 5/1987 | Hargis | |
| 4,668,221 A | 5/1987 | Luther | |
| 4,671,796 A | 6/1987 | Groshong et al. | |
| 4,673,394 A | 6/1987 | Fenton, Jr. et al. | |
| 4,684,365 A | 8/1987 | Reinicke | |
| 4,685,447 A | 8/1987 | Iversen et al. | |
| 4,685,905 A | 8/1987 | Jeanneret nee Aab | |
| 4,692,146 A | 9/1987 | Hilger | |
| 4,695,273 A | 9/1987 | Brown | |
| 4,697,595 A | 10/1987 | Breyer et al. | |
| 4,701,166 A | 10/1987 | Groshong et al. | |
| 4,704,103 A | 11/1987 | Stober et al. | |
| 4,718,894 A | 1/1988 | Lazorthes | |
| 4,743,231 A | 5/1988 | Kay et al. | |
| 4,753,640 A | 6/1988 | Nichols et al. | |
| 4,755,173 A | 7/1988 | Konopka et al. | |
| 4,760,837 A | 8/1988 | Petit | |
| 4,762,517 A | 8/1988 | McIntyre et al. | |
| 4,772,270 A | 9/1988 | Wiita et al. | |
| 4,772,276 A | 9/1988 | Wiita et al. | |
| 4,773,552 A | 9/1988 | Boege et al. | |
| 4,778,452 A | 10/1988 | Moden et al. | |
| 4,781,680 A | 11/1988 | Redmond et al. | |
| 4,781,685 A | 11/1988 | Lehmann et al. | |
| 4,802,885 A | 2/1989 | Weeks et al. | |
| 4,820,273 A | 4/1989 | Reinicke | |
| 4,840,615 A | 6/1989 | Hancock et al. | |
| 4,848,346 A | 7/1989 | Crawford | |
| 4,857,053 A | 8/1989 | Dalton | |
| 4,861,341 A | 8/1989 | Woodburn | |
| 4,863,470 A | 9/1989 | Carter | |
| 4,886,501 A | 12/1989 | Johnston et al. | |
| 4,915,690 A | 4/1990 | Cone et al. | |
| 4,928,298 A | 5/1990 | Tanaka et al. | |
| 4,929,236 A | 5/1990 | Sampson | |
| 4,966,583 A | 10/1990 | Debbas | |
| 4,973,319 A | 11/1990 | Melsky | |
| 5,009,644 A | 4/1991 | McDonald | |
| 5,013,298 A | 5/1991 | Moden et al. | |
| 5,041,098 A | 8/1991 | Loiterman et al. | |
| 5,044,955 A | 9/1991 | Jagmin | |
| 5,045,060 A | 9/1991 | Melsky et al. | |
| 5,084,015 A | 1/1992 | Moriuchi | |
| 5,085,216 A | 2/1992 | Henley, Jr. et al. | |
| 5,090,066 A | 2/1992 | Schoepe et al. | |
| 5,092,849 A | 3/1992 | Sampson | |
| 5,108,317 A | 4/1992 | Beinhaur et al. | |
| 5,108,377 A | 4/1992 | Cone et al. | |
| 5,112,301 A | 5/1992 | Fenton, Jr. et al. | |
| 5,112,303 A | 5/1992 | Pudenz et al. | |
| 5,137,529 A * | 8/1992 | Watson et al. | 604/891.1 |
| 5,147,483 A | 9/1992 | Melsky et al. | |
| 5,152,753 A | 10/1992 | Laguette et al. | |
| 5,156,600 A | 10/1992 | Young | |
| 5,167,629 A | 12/1992 | Vertenstein et al. | |
| 5,167,638 A | 12/1992 | Felix et al. | |
| 5,176,653 A | 1/1993 | Metals et al. | |
| 5,176,662 A | 1/1993 | Bartholomew et al. | |
| 5,178,612 A | 1/1993 | Fenton, Jr. | |
| 5,185,003 A | 2/1993 | Brethauer | |
| 5,189,690 A | 2/1993 | Samuel | |
| 5,193,106 A | 3/1993 | DeSena | |
| 5,195,122 A | 3/1993 | Fabian | |
| 5,201,715 A | 4/1993 | Masters | |
| 5,203,777 A | 4/1993 | Lee | |
| 5,213,574 A | 5/1993 | Tucker | |
| 5,215,537 A | 6/1993 | Lynn et al. | |
| 5,222,499 A | 6/1993 | Allen et al. | |
| D337,637 S * | 7/1993 | Tucker | |
| 5,224,938 A | 7/1993 | Fenton, Jr. | |
| 5,281,205 A | 1/1994 | McPherson | |
| 5,295,658 A | 3/1994 | Atkinson et al. | |
| 5,299,253 A | 3/1994 | Wessels | |
| 5,309,863 A | 5/1994 | Leeb, Jr. | |
| 5,318,545 A | 6/1994 | Tucker | |
| 5,320,100 A | 6/1994 | Herweck et al. | |
| 5,328,480 A | 7/1994 | Melker et al. | |
| 5,332,398 A | 7/1994 | Miller et al. | |
| 5,338,398 A | 8/1994 | Szwejkowski et al. | |
| 5,352,204 A | 10/1994 | Ensminger | |
| 5,360,407 A | 11/1994 | Leonard | |
| 5,383,233 A | 1/1995 | Russell | |
| 5,383,858 A | 1/1995 | Reilly et al. | |
| D355,240 S * | 2/1995 | Gladfelter et al. | |
| 5,387,192 A | 2/1995 | Glantz et al. | |
| 5,394,457 A | 2/1995 | Leibinger et al. | |
| 5,397,329 A | 3/1995 | Allen | |
| 5,405,402 A | 4/1995 | Dye et al. | |
| 5,417,565 A | 5/1995 | Long | |
| 5,417,656 A | 5/1995 | Ensminger et al. | |
| 5,423,334 A | 6/1995 | Jordan | |
| 5,456,698 A | 10/1995 | Byland et al. | |
| 5,476,460 A | 12/1995 | Montalvo | |
| 5,476,880 A | 12/1995 | Cooke et al. | |
| 5,484,402 A | 1/1996 | Saravia et al. | |
| 5,507,813 A | 4/1996 | Dowd et al. | |
| 5,509,805 A | 4/1996 | Jagmin | |
| 5,513,637 A | 5/1996 | Twiss et al. | |
| 5,556,381 A | 9/1996 | Ensminger et al. | |
| 5,558,641 A | 9/1996 | Glantz et al. | |
| 5,607,407 A | 3/1997 | Tolkoff et al. | |
| 5,613,945 A | 3/1997 | Cai et al. | |
| 5,620,419 A | 4/1997 | Lui et al. | |
| 5,637,102 A | 6/1997 | Tolkoff et al. | |
| 5,662,612 A | 9/1997 | Niehoff | |
| 5,676,146 A | 10/1997 | Scarborough | |
| 5,695,490 A | 12/1997 | Flaherty et al. | |
| 5,702,128 A | 12/1997 | Maxim et al. | |
| 5,704,915 A | 1/1998 | Melsky et al. | |
| 5,709,668 A | 1/1998 | Wacks | |
| 5,713,858 A | 2/1998 | Heruth et al. | |
| 5,713,859 A | 2/1998 | Finch, Jr. et al. | |
| 5,718,382 A | 2/1998 | Jaeger | |
| 5,718,682 A | 2/1998 | Tucker | |
| 5,725,507 A | 3/1998 | Petrick | |
| 5,733,400 A | 3/1998 | Gore et al. | |
| 5,743,873 A | 4/1998 | Cai et al. | |
| 5,743,891 A | 4/1998 | Tolkoff et al. | |
| 5,773,552 A | 6/1998 | Hutchings et al. | |
| 5,792,104 A | 8/1998 | Speckman et al. | |
| 5,792,116 A | 8/1998 | Berg et al. | |
| 5,824,071 A | 10/1998 | Nelson et al. | |
| 5,833,654 A | 11/1998 | Powers et al. | |
| 5,843,069 A | 12/1998 | Butler et al. | |
| 5,853,394 A | 12/1998 | Tolkoff et al. | |
| 5,868,702 A | 2/1999 | Stevens et al. | |
| 5,895,424 A | 4/1999 | Steele, Sr. et al. | |
| 5,913,998 A | 6/1999 | Butler et al. | |
| 5,928,197 A | 7/1999 | Niehoff | |
| 5,931,829 A | 8/1999 | Burbank et al. | |
| 5,944,688 A | 8/1999 | Lois | |
| 5,944,712 A | 8/1999 | Frassica et al. | |
| 5,947,953 A | 9/1999 | Ash et al. | |
| 5,951,512 A | 9/1999 | Dalton | |
| 5,951,522 A | 9/1999 | Rosato et al. | |
| 5,968,011 A | 10/1999 | Larsen et al. | |

| | | | | | | |
|---|---|---|---|---|---|---|
| 5,970,162 | A | 10/1999 | Kawashima et al. | D574,950 S | 8/2008 | Zawacki et al. |
| 5,989,216 | A | 11/1999 | Johnson et al. | 7,413,564 B2 * | 8/2008 | Morris et al. |
| 5,989,239 | A | 11/1999 | Finch et al. | 7,445,614 B2 * | 11/2008 | Bunodiere et al. |
| 5,997,524 | A | 12/1999 | Burbank et al. | 7,465,847 B2 * | 12/2008 | Fabian |
| 6,007,516 | A | 12/1999 | Burbank et al. | 2001/0053889 A1 | 12/2001 | Marggi et al. |
| 6,013,058 | A | 1/2000 | Prosl et al. | 2001/0056266 A1 | 12/2001 | Tallarida et al. |
| 6,017,331 | A | 1/2000 | Watts et al. | 2002/0138068 A1 | 9/2002 | Watson et al. |
| 6,022,335 | A | 2/2000 | Ramadan | 2003/0130627 A1 | 7/2003 | Smith et al. |
| 6,033,389 | A | 3/2000 | Cornish | 2003/0139812 A1 | 7/2003 | Garcia et al. |
| 6,039,712 | A | 3/2000 | Fogarty et al. | 2003/0181878 A1 | 9/2003 | Tallarida et al. |
| 6,077,756 | A | 6/2000 | Lin et al. | 2004/0020462 A1 | 2/2004 | Sauler et al. |
| 6,086,555 | A | 7/2000 | Eliasen | 2004/0044306 A1 | 3/2004 | Lynch et al. |
| 6,090,066 | A | 7/2000 | Schnell | 2004/0056266 A1 | 3/2004 | Suh et al. |
| 6,113,572 | A | 9/2000 | Gailey et al. | 2004/0106891 A1 | 6/2004 | Langan et al. |
| 6,120,492 | A | 9/2000 | Finch et al. | 2004/0158207 A1 | 8/2004 | Hunn et al. |
| 6,161,033 | A | 12/2000 | Kuhn | 2004/0167543 A1 | 8/2004 | Mazzocchi et al. |
| 6,171,198 | B1 | 1/2001 | Lizama Troncoso et al. | 2004/0176743 A1 | 9/2004 | Morris et al. |
| 6,171,298 | B1 | 1/2001 | Matsuura et al. | 2004/0199129 A1 | 10/2004 | DiMatteo |
| 6,190,352 | B1 | 2/2001 | Haarala et al. | 2004/0199220 A1 | 10/2004 | Cantlon |
| 6,193,684 | B1 | 2/2001 | Burbank et al. | 2004/0204692 A1 | 10/2004 | Eliasen |
| 6,198,807 | B1 | 3/2001 | DeSena | 2005/0049553 A1 | 3/2005 | Triplett et al. |
| 6,213,973 | B1 | 4/2001 | Eliasen et al. | 2005/0075614 A1 | 4/2005 | Bunodiere et al. |
| 6,251,059 | B1 | 6/2001 | Apple et al. | 2005/0113806 A1 | 5/2005 | DeCarvalho et al. |
| D445,175 | S * | 7/2001 | Bertheas | 2005/0152841 A1* | 7/2005 | Sayre et al. ............... 424/9.4 |
| 6,269,148 | B1 | 7/2001 | Jessop et al. | 2005/0182857 A1 | 8/2005 | Kong |
| 6,287,293 | B1 * | 9/2001 | Jones et al. ................ 604/891.1 | 2005/0209573 A1 | 9/2005 | Brugger et al. |
| 6,290,677 | B1 | 9/2001 | Arai et al. | 2005/0215874 A1 | 9/2005 | Wang et al. |
| 6,305,413 | B1 | 10/2001 | Fischer et al. | 2005/0241203 A1 | 11/2005 | Lizotte et al. |
| D450,115 | S * | 11/2001 | Bertheas | 2005/0256500 A1 | 11/2005 | Fujii |
| 6,355,021 | B1 | 3/2002 | Nielsen et al. | 2005/0283119 A1 | 12/2005 | Uth et al. |
| 6,356,782 | B1 | 3/2002 | Sirimanne et al. | 2006/0009788 A1 | 1/2006 | Freeman et al. |
| 6,361,557 | B1 | 3/2002 | Gittings et al. | 2006/0116648 A1 | 6/2006 | Hamatake |
| 6,398,764 | B1 | 6/2002 | Finch, Jr. et al. | 2006/0173410 A1 | 8/2006 | Moberg et al. |
| 6,419,680 | B1 | 7/2002 | Cosman et al. | 2006/0178647 A1 | 8/2006 | Stats |
| 6,478,783 | B1 * | 11/2002 | Moorehead ............... 604/288.02 | 2006/0217659 A1 | 9/2006 | Patton |
| 6,494,867 | B1 | 12/2002 | Elver et al. | 2006/0224129 A1 | 10/2006 | Beasley et al. |
| 6,500,155 | B2 | 12/2002 | Sasso | 2006/0247584 A1* | 11/2006 | Sheetz et al. ............. 604/288.02 |
| 6,503,228 | B1 | 1/2003 | Li et al. | 2006/0253076 A1 | 11/2006 | Butts et al. |
| 6,527,754 | B1 | 3/2003 | Tallarida et al. | 2006/0264898 A1 * | 11/2006 | Beasley et al. ................ 604/506 |
| 6,537,255 | B1 | 3/2003 | Raines | 2007/0049876 A1 | 3/2007 | Patton |
| 6,582,418 | B1 | 6/2003 | Verbeek et al. | 2007/0055290 A1 | 3/2007 | Lober |
| 6,613,002 | B1 | 9/2003 | Clark et al. | 2007/0073250 A1 | 3/2007 | Schneiter |
| 6,613,662 | B2 | 9/2003 | Wark et al. | 2007/0078391 A1 | 4/2007 | Wortley et al. |
| 6,632,217 | B2 | 10/2003 | Harper et al. | 2007/0078416 A1 | 4/2007 | Eliasen |
| 6,652,486 | B2 | 11/2003 | Bialecki et al. | 2007/0078432 A1 | 4/2007 | Halseth et al. |
| 6,652,503 | B1 | 11/2003 | Bradley | 2007/0083156 A1 | 4/2007 | Muto et al. |
| 6,676,633 | B2 | 1/2004 | Smith et al. | 2007/0149920 A1 | 6/2007 | Michels et al. |
| 6,697,664 | B2 | 2/2004 | Kienzle, III et al. | 2007/0149921 A1 | 6/2007 | Michels et al. |
| 6,719,721 | B1 | 4/2004 | Okazaki et al. | 2007/0161958 A1 | 7/2007 | Glenn |
| 6,738,531 | B1 | 5/2004 | Funahashi | 2007/0185462 A1 | 8/2007 | Byrum |
| 6,826,257 | B2 | 11/2004 | Sayre et al. | 2007/0191773 A1 | 8/2007 | Wojcik |
| 6,852,106 | B2 | 2/2005 | Watson et al. | 2007/0208313 A1 | 9/2007 | Conlon et al. |
| 6,878,136 | B2 | 4/2005 | Fleury et al. | 2007/0219510 A1 | 9/2007 | Zinn et al. |
| 6,878,137 | B2 | 4/2005 | Benchetrit | 2007/0233017 A1* | 10/2007 | Zinn et al. ................ 604/288.01 |
| 6,997,914 | B2 | 2/2006 | Smith et al. | 2007/0233018 A1 | 10/2007 | Bizup et al. |
| 7,016,456 | B2 | 3/2006 | Basu et al. | 2007/0270770 A1 | 11/2007 | Bizup |
| 7,072,704 | B2 * | 7/2006 | Bucholz | 2007/0276344 A1 | 11/2007 | Bizup et al. |
| 7,127,040 | B2 * | 10/2006 | Sayre et al. | 2007/0299408 A1 | 12/2007 | Alferness et al. |
| 7,191,011 | B2 * | 3/2007 | Cantlon | 2008/0004642 A1 | 1/2008 | Birk et al. |
| 7,214,207 | B2 * | 5/2007 | Lynch et al. | 2008/0008654 A1 | 1/2008 | Clarke et al. |
| 7,214,215 | B2 * | 5/2007 | Heinzerling et al. | 2008/0015701 A1 | 1/2008 | Garcia et al. |
| 7,223,257 | B2 * | 5/2007 | Shubayev et al. | 2008/0039820 A1 | 2/2008 | Sommers et al. |
| 7,229,417 | B2 * | 6/2007 | Foerster et al. | 2008/0048855 A1 | 2/2008 | Berger |
| 7,235,067 | B2 * | 6/2007 | Morris et al. | 2008/0108949 A1* | 5/2008 | Beasley et al. ................ 604/180 |
| D546,440 | S * | 7/2007 | Burnside | 2008/0140025 A1 | 6/2008 | Sheetz et al. |
| 7,252,469 | B2 * | 8/2007 | Zaluzec et al. | 2008/0208236 A1 | 8/2008 | Hobbs et al. |
| 7,252,649 | B2 * | 8/2007 | Sherry | 2008/0319399 A1 * | 12/2008 | Schweikert et al. .......... 604/175 |
| 7,261,705 | B2 * | 8/2007 | Edoga et al. | 2009/0024024 A1 | 1/2009 | Zinn |
| D554,253 | S * | 10/2007 | Kornerup | 2009/0024098 A1 | 1/2009 | Bizup et al. |
| 7,275,682 | B2 | 10/2007 | Excoffier et al. | 2009/0118683 A1 | 5/2009 | Hanson et al. |
| D556,153 | S * | 11/2007 | Burnside | 2009/0156928 A1 | 6/2009 | Evans et al. |
| 7,318,816 | B2 * | 1/2008 | Bobroff et al. | 2009/0204072 A1 * | 8/2009 | Amin et al. ................... 604/116 |
| 7,318,818 | B2 * | 1/2008 | Yashiro et al. | | | |
| 7,322,953 | B2 * | 1/2008 | Redinger | | FOREIGN PATENT DOCUMENTS | |
| D562,443 | S | 2/2008 | Zinn et al. | WO | WO 8600213 A1 | 1/1986 |
| 7,331,130 | B2 * | 2/2008 | Schweikert | WO | WO 9305730 A1 | 4/1993 |
| 7,331,948 | B2 * | 2/2008 | Skarda | WO | WO 9701370 A1 | 1/1997 |
| 7,333,013 | B2 | 2/2008 | Berger | WO | WO 9942166 A1 | 8/1999 |
| 7,347,838 | B2 * | 3/2008 | Kulli | WO | WO 0033901 A1 | 6/2000 |

| | | |
|---|---|---|
| WO | WO 0247549 A1 | 6/2002 |
| WO | WO 2004004800 A2 | 1/2004 |
| WO | WO 2006096686 A1 | 9/2006 |
| WO | WO2006/116438 A2 | 11/2006 |
| WO | WO 2007079024 A2 | 7/2007 |
| WO | WO 2007136538 A2 | 11/2007 |
| WO | WO 2008008126 A2 | 1/2008 |
| WO | WO 2008019236 A1 | 2/2008 |
| WO | WO 2008048361 A1 | 4/2008 |
| WO | WO 2008063226 A2 | 5/2008 |
| WO | WO 2008157763 A1 | 12/2008 |
| WO | WO 2009012385 A1 | 1/2009 |
| WO | WO 2009012395 A1 | 1/2009 |
| WO | WO 2009035582 A1 | 3/2009 |
| WO | WO 2009046439 A2 | 4/2009 |

OTHER PUBLICATIONS

Written Opinion dated Dec. 1, 2008; PCT/US2008/070330 (5 pages).
Bard Access System product drawings representative of the BARD Access System products on the market on or around Mar. 1995 as indicated by the BARD Access Systems Mar. 21, 1995 Product Release to Market form for "M.R.I. Port with 8 Fr. ChronoFlex® Catheter," "M.R.I. Port with 8 Fr. ChronoFlex Catheter with Intro-Eze™," "M.R.I. Port with 8 Fr. Chrono-Flex Catheter and Peel Apart," "M.R.I. Port with 8 Fr. ChronoFlex Catheter Demo Kit," 6 pages.
BioEnterics® LAP-BAND® "Adjustable Gastric Banding System" by Inamed Health, Product Brochure, Dec. 2003, 22 pages.
Cardiovascular and Interventional Radiology, Review Article, "Central Venous Access Catheters: Radiological Management of Complications," by U.K. Teichgraber et al., published online Jul. 31, 2003, 13 pages.
European Patent Office Communication, dated Dec. 15, 2005, for Application No. 99 964 086.5—1257, Applicant STD Manufacturing, Inc., 9 pages.
European Patent Office Communication, dated Mar. 1, 2005, for EP Application No. 99 964 086.5—1257, Applicant STD Manufacturing, Inc., 4 pages.
European Patent Office Communication, dated Mar. 30, 2005, for Application No. 99 964 086.5—1257, Applicant STD Manufacturing, Inc., 3 pages.
European Patent Office Communication, dated Sep. 2, 2008, for Application No. 06 751 411.7-1526, Applicant C.R. Bard, Inc., 4 pages.
LaMaitre Vascular "Port Implantations: using the OptiLock Implantable Port," product information, available at http://www.lemaitre.com/specs_pop.asp, last accessed Apr. 2003, 14 pages.
LAP-BAND AP™ "System with Adjustable Gastric Banding system with OMNIFORM™ Design," Product Brochure, Jul. 2007, 16 pages.
LAP-BAND® "Adjustable Gastric Banding System" by BioEnterics Corporation, Product Brochure, 12 pages.
LAP-BAND® System Fact Sheet, ©2007 Allergan, Inc., 2 pages.
MedComp "PortCT Technology", display at SIR Conference, Toronto, Canada, (Mar. 2006), 1 page.
Nucleus Cochlear Implant Systems; User Manual for the ESPrit 3G speech processor and accessories, available at http://www.cochlearamericas.com/PDFs/UserManualSprint.pdf, Issue 2, Dec. 2001, 2 pages.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PORT-A-CATH® "Implantable Epidural, Aterial and Peritonial Access Systems," Internet Product Listing of Nov. 19, 2000 archived at http://web.archive.org/web/20001119035900/www.deltec.com/cPacspl.htm, last accessed Oct. 17, 2009, 2 pages.
PORT-A-CATH® "Many PORT-A-CATH® System Choices," Product Brochure, ©1996 SIMS Deltec, Inc., 5 pages.
PORT-A-CATH® "Single-lumen Implantable Vascular Access Systems," Product Specifications, 2004 Smith Medical, 4 pages.

Rappolt, Richard T., et al., "Radiopaque Codification and X-ray identification of Ingested Drugs," Ingestive Radioiogy, May-Jun. 1966, 4 pages.
Shah, Tilak M. "Radiopaque Polymer Formulations for Medical Devices." Medical Device and Diagnostic Industry, Mar. 2000, 6 pages.
Urquiola, Javier, et al., "Using Lead Foil as a Radiopaque Marker for Computerized Tomography Imaging When Implant Treatment Planning," The Journal of Prosthetic Dentistry, vol. 77, No. 2, Feb. 1997, pp. 227-228.
PCT/US06/008022 International Search Report, mailed Jul. 5, 2006, 2 pages.
PCT/US06/015695 International Search Report, mailed Jan. 11, 2007, 6 pages.
PCT/US06/49007 International Search Report, mailed Oct. 1, 2007, 2 pages.
PCT/US06/49007 Written Opinion, mailed Oct. 1, 2007, 4 pages.
PCT/US07/006776 International Search Report, mailed Dec. 18, 2007, 1 page.
PCT/US07/006776 Written Opinion, mailed Dec. 18, 2007, 3 pages.
PCT/US08/067679 International Search Report, mailed Sep. 30, 2008, 3 pages.
PCT/US08/067679 Written Opinion, mailed Sep. 30, 2008, 4 pages.
PCT/US08/070345 International Search Report, mailed Dec. 1, 2008, 5 pages.
PCT/US08/070345 Written Opinion, mailed Dec. 1, 2008, 6 pages.
U.S. Appl. No. 10/374,000, Advisory Action, mailed Jan. 23, 2007, 3 pages.
U.S. Appl. No. 10/374,000, Office Action, mailed Aug. 28, 2007, 8 pages.
U.S. Appl. No. 10/374,000, Office Action, mailed Feb. 13, 2006, 7 pages.
U.S. Appl. No. 10/374,000, Office Action, mailed Feb. 28, 2007, 8 pages.
U.S. Appl. No. 10/374,000, Office Action, mailed Jul. 28, 2006, 8 pages.
U.S. Appl. No. 10/374,000, Office Action, mailed Mar. 20, 2008, 6 pages.
U.S. Appl. No. 10/374,000, Office Action, mailed May 20, 2009, 9 pages.
U.S. Appl. No. 10/374,000, Office Action, mailed Sep. 30, 2008, 7 pages.
U.S. Appl. No. 10/374,000, Response to Office Action, filed Dec. 28, 2006, 9 pages.
U.S. Appl. No. 10/374,000, Response to Office Action, filed Jun. 20, 2008, 8 pages.
U.S. Appl. No. 10/374,000, Response to Office Action, filed Mar. 30, 2009, 11 pages.
U.S. Appl. No. 10/374,000, Response to Office Action, filed May 12, 2006, 7 pages.
U.S. Appl. No. 10/374,000, Response to Office Action, filed May 29, 2007, 2006, 11 pages.
U.S. Appl. No. 10/374,000, Response to Office Action, filed Oct. 31, 2007, 8 pages.
U.S. Appl. No. 10/374,000, Response to Office Action, filed Sep. 21, 2009, 13 pages.
U.S. Appl. No. 11/320,223, Office Action, mailed Feb. 13, 2008, 11 pages.
U.S. Appl. No. 11/320,223, Office Action, mailed Sep. 18, 2008, 7 pages.
U.S. Appl. No. 11/368,954, Preliminary Amendment, filed Dec. 19, 2007, 9 pages.
U.S. Appl. No. 11/380,124, Office Action, mailed Jan. 16, 2009, 10 pages.
U.S. Appl. No. 11/725,287, Office Action, mailed Jun. 12, 2009, 5 pages.
U.S. Appl. No. 11/725,287, Office Action, mailed Dec. 3, 2008, 7 pages.

U.S. Appl. No. 12/143,377, Office Action, mailed Oct. 19, 2009, 9 pages.
U.S. Appl. No. 12/143,377, Office Action, mailed Apr. 27, 2009, 6 pages.
U.S. Appl. No. 29/284,454, filed Sep. 7, 2007, entitled "Implantable Port Device," issued Aug. 12, 2008 as U.S. Patent No. D574,950, 8 pages.

U.S. Appl. No. 29/284,456, filed Sep. 7, 2007 entitled "Implantable Port Device," 8 pages.
U.S. Appl. No. 60/658,518, filed Mar. 4, 2005, publicly accessible Oct. 5, 2006, 62 pages.

* cited by examiner

VENOUS ACCESS PORT ASSEMBLY WITH X-RAY DISCERNABLE INDICIA

CROSS-REFERENCE TO RELATED APPLICATION

This claims the benefit of U.S. Provisional Patent Application Ser. No. 60/961,133 filed Jul. 19, 2007.

FIELD OF THE INVENTION

This relates to the field of medical devices and more particularly to venous access ports for the infusion of fluids into the patient and/or withdrawal of fluids from the patient.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574 and 5,637,102.

It is desired to provide a venous access port assembly that provides for a radiologist, radiology technologist, nurse and ultimately a medical practitioner to be able to discern an important property of the port assembly after the port assembly has been implanted into a patient.

BRIEF SUMMARY OF THE INVENTION

The present invention is related to a venous access port having a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. The invention is the incorporation of X-ray discernable indicia onto a venous access port that is discernible under X-ray examination to provide information concerning the nature or key attribute of the venous access port, so that the practitioner, subsequent to the date of implantation thereof, can determine that nature or key attribute under X-ray examination. One such key attribute in particular would be for example that the venous access port is rated to be used for power injection such as of contrast fluid, wherein for example the letters "CT" (for "computed tomography", or "contrast enhanced computed tomography") would be provided that are of radiopaque material, or are cutouts through radiopaque material. The attribute in this example is the property of the port's being adapted to withstand high pressures that are used for injection of contrast fluid into a patient, and the letters "CT" would be understood in medical practice to indicate that the port is suitable for the high pressure injection of contrast fluid.

In one embodiment, a disc of radiopaque material includes cutouts therethrough of letters "CT" (although other indicia may be utilized) through the body of the disc. In another embodiment, discrete letters "CT" (although other indicia may be utilized) are provided of radiopaque material. With either embodiment, the disc or letters may be insert molded within the housing base bottom wall, or they may be affixed to the bottom surface of the housing base, preferably within complementary recesses thereinto, in such a manner that the letters "CT" are readable from above the port assembly in an X-ray.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A recess 26 is seen to be provided along both sides of discharge port 16, facilitating insertion of the discharge port 16 into the catheter lumen and providing a clearance for a locking sleeve or clamp (not shown) utilized to compress the catheter lumen wall against the exterior surface of the discharge port 16 for assured sealed connection of the catheter with the port assembly 10.

With reference now to FIGS. 3 to 7, the interior of the port assembly 10 is shown to provide an interior reservoir 22. Housing 12 is shown to include a housing base 28 of needle-impenetrable material that includes a well 30 having a bottom floor 32 and side walls 34 that define the interior reservoir 22 beneath septum 14. Bottom floor 32 may be convex or elevated (not shown) toward the center of the reservoir, if desired. Housing base 28 includes a base flange 36 extending radially outwardly from the bottom of well 30, and base flange 36 includes openings 38,40 that serve to enable suturing to the patient upon placement of the venous access port and the attached catheter into the patient.

Figure 1:
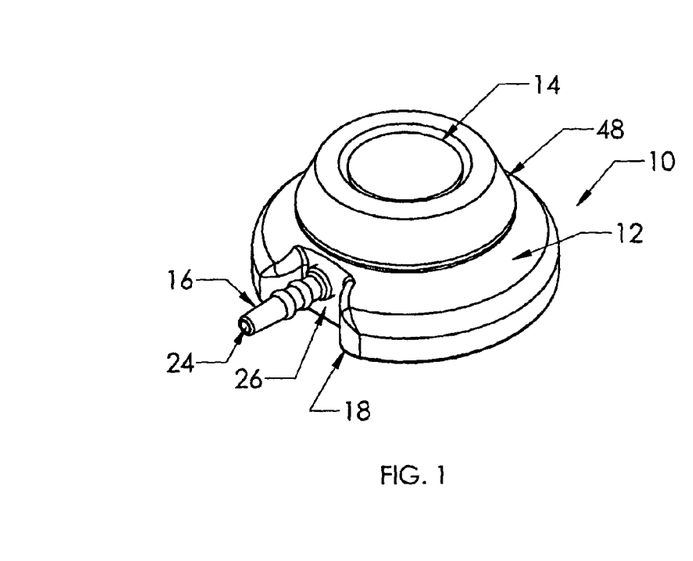
FIGS. 1 and 2 are an isometric view and a plan view of the venous access port of the present invention.
Figure 2:
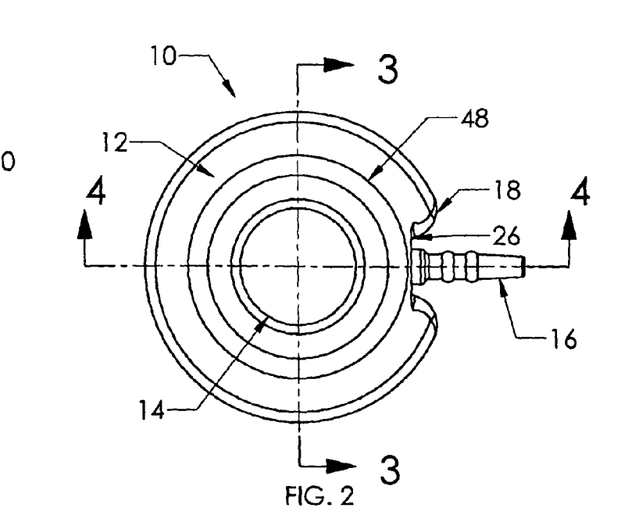
Figure 3:
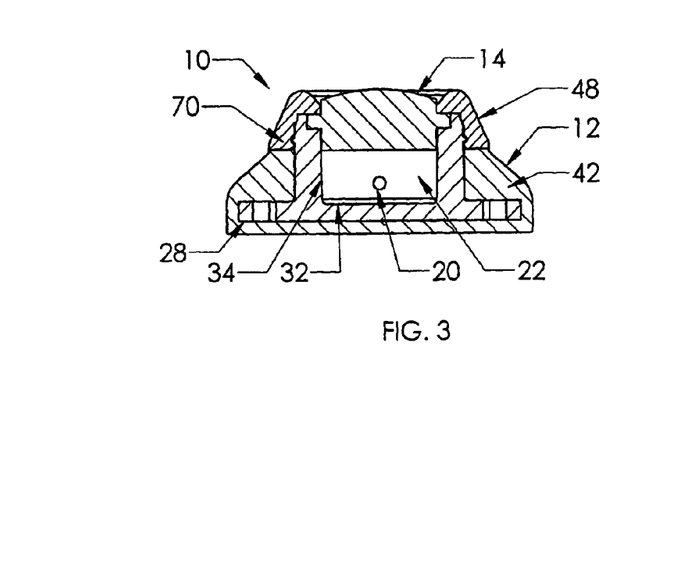
FIGS. 3 and 4 are cross-section views of the port of FIGS. 1 and 2 taken along lines 3-3 and lines 4-4 of FIG. 1, respectively.
Figure 4:
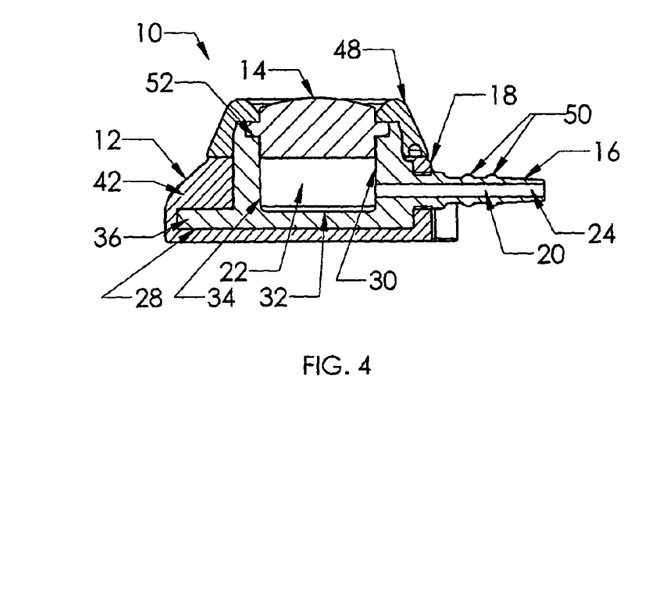
Figure 5:
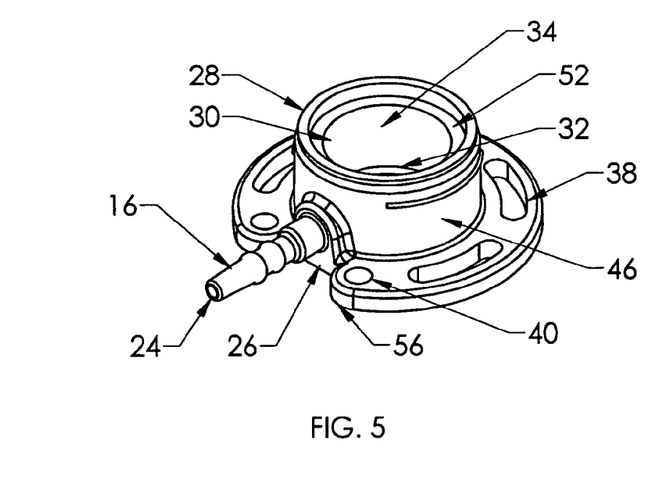
FIG. 5 is an isometric view of the needle-impenetrable housing base of the venous access port of FIG. 1.
Figure 6:
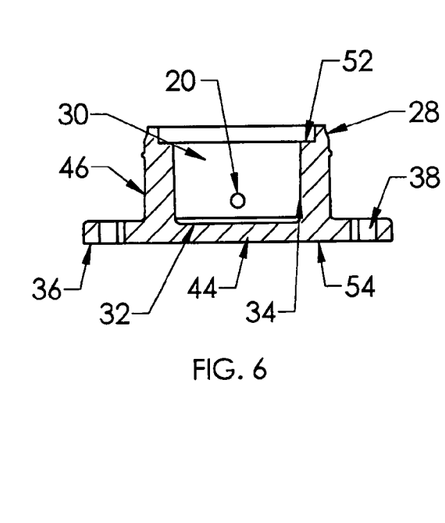
FIGS. 6 and 7 are transverse cross-sectional and longitudinal cross-sectional views of the housing base of FIG. 5.

As shown in FIGS. 3 and 4, a skirt 42 is overmolded about housing base 28 and may be of silicone elastomer. It is seen that skirt 42 encapsulates the outer surfaces of the bottom wall 44 and the bottom portion of the side walls 46 of housing base 28, and is shown to fill in the suture holes 38,40; but since the material is silicone elastomer, suturing is possible since the suturing needle can easily be inserted through the material of skirt 42 and through the suture holes, and thereafter the filled openings provide minimal opportunity for ingrowth of patient tissue into the openings.

Figure 7:
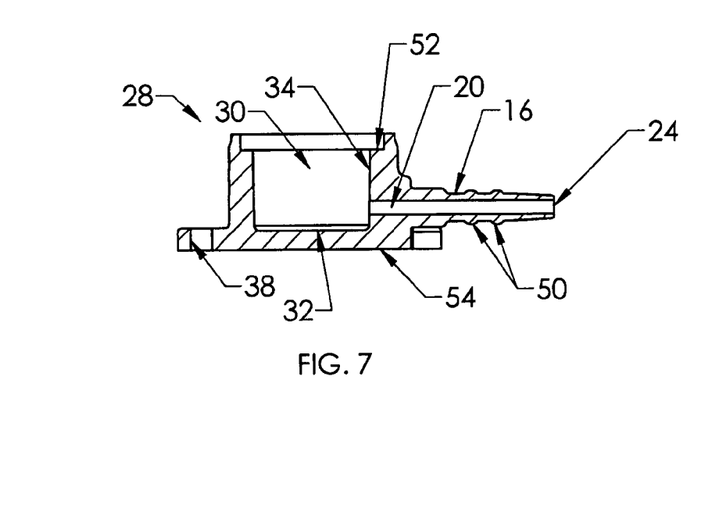

Also seen in FIGS. 1 to 4 is cap 48, which secures to housing base 28 to in turn secure septum 14 in position in the port assembly 10. Preferably, skirt 42 is insert molded onto base flange 36 of housing base 28 before cap 48 is secured to the upper portion of housing base 28 to secure the septum in position. It is seen in FIGS. 4 and 7 that discharge port 16 is integral with housing base 28 as is preferable. Discharge port 16 is shown to have a pair of annular ridges 50 that facilitate with the mechanical connection of the catheter proximal end with the port assembly 10. Housing base 28 includes a septum seat 52 extending into the top of well 30, into which a flange of the septum will be seated, preferably under radially inward compression. Housing base 28 has a bottom outer surface 54.

Figure 8:
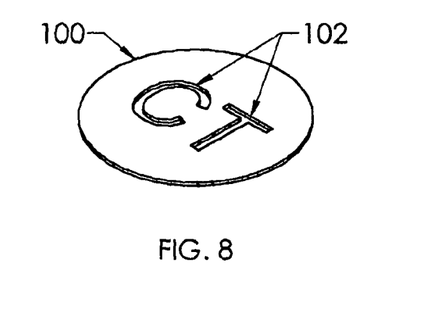
FIG. 8 is an isometric view of a first embodiment of X-ray discernable indicia, being a disc of radiopaque material having letters cut out thereof.
Figure 9:
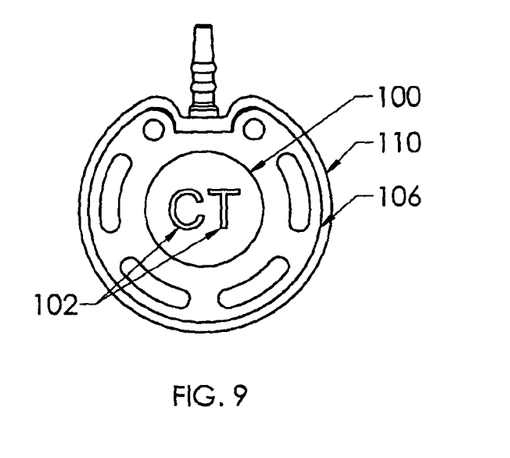
FIGS. 9 to 11 are bottom, cross-sectional and top views of the port assembly of FIGS. 1 to 7 having the disc of FIG. 8 affixed to the housing base of FIGS. 6 and 7 and within a shallow recess into its bottom surface, with silicone covering molded thereover, and the indicia being shown in dashed lines in FIGS. 9 and 11.
Figure 10:
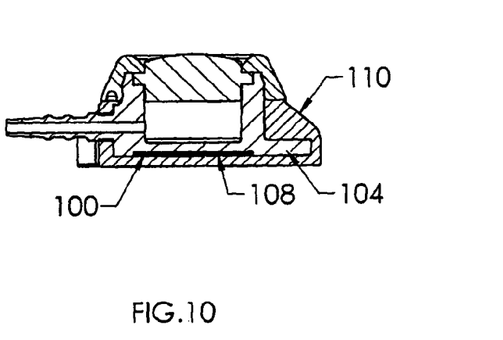

FIG. 8 shows a first embodiment of a component of radiopaque material of the present invention in the form of a disc 100, such as of titanium. Cutouts 102 are formed through the disc body, shown in FIG. 8 as the alphabetical letters "CT". Disc 100 is affixed to the bottom surface 104 of housing base 106 in FIGS. 9 and 10, preferably within a complementary shallow recess 108 thereinto. A skirt 110 of silicone material is molded over the housing base, and is transparent so that the letters "CT" are visible from below but in a mirror-image orientation on the bottom outer surface of the housing base (FIG. 9) so that the indicia would appear as "CT" when the X-ray is viewed (FIG. 11), easily discerned by the radiologist or technologist. Centering of the indicia within the region directly beneath the reservoir and septum minimizes any obscuring by the structure of the venous access port assembly, and the indicia may also be easily discernable should the port assembly be at an angle from the horizontal plane of the X-ray.

Figure 11:
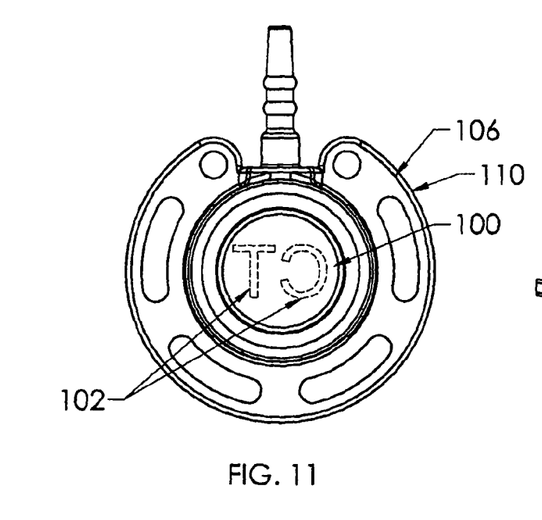
Figure 12:
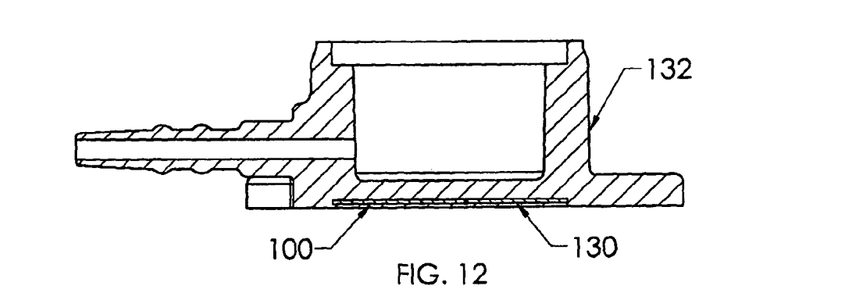
FIG. 12 is a cross-sectional view of an alternate embodiment of housing base having the disc of FIG. 8 insert molded embedded within the bottom wall of the base.

In FIG. 12, an alternate embodiment of the present invention is shown, in which the disc 100 of FIG. 8 is embedded within the thickness of the bottom wall 130 of the housing base 132, and the X-ray would appear very similar to that shown in FIG. 11 but the indicia would not be visible from below the housing base or the port assembly.

Figure 13:
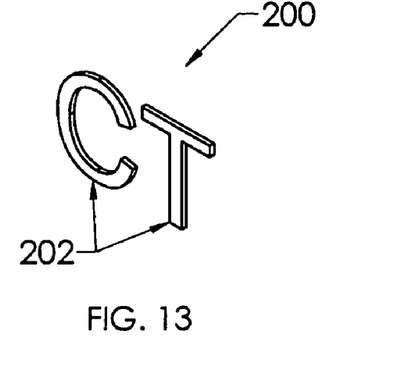
FIG. 13 is an isometric view of a second embodiment of radiopaque indicia, comprising a set of discrete letters of radiopaque material.
Figure 14:
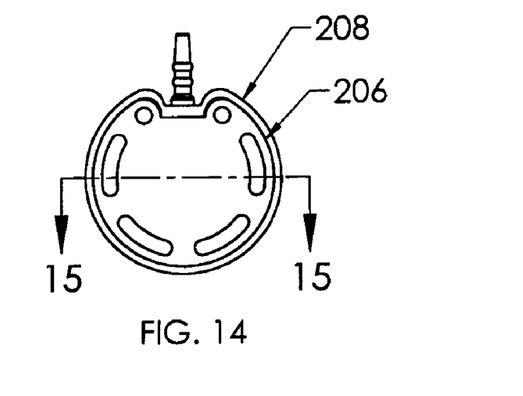
FIGS. 14 and 15 are a bottom view and a cross-sectional view of a port assembly of FIGS. 1 to 7 having the discrete letters of FIG. 13 insert molded into the bottom wall of the housing base, with FIG. 15 taken along lines 15-15 of FIG. 13.
Figure 15:
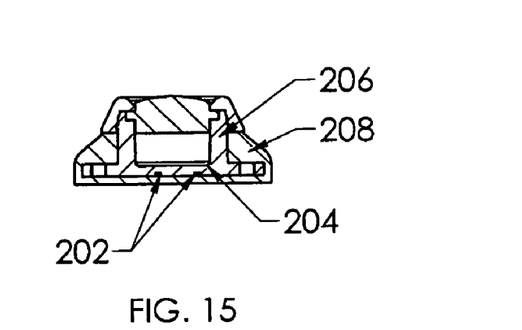
Figure 16:
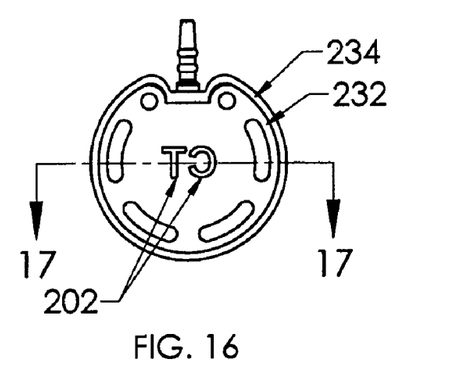
FIGS. 16 to 18 are a bottom view, cross-sectional view and an isometric bottom view of a port assembly of FIGS. 1 to 7 having the discrete letters of FIG. 13 affixed to the bottom surface of the housing base, shown within respective recesses thereinto, with a silicone covering molded thereover, with FIG. 17 taken along lines 17-17 of FIG. 16.
Figure 17:
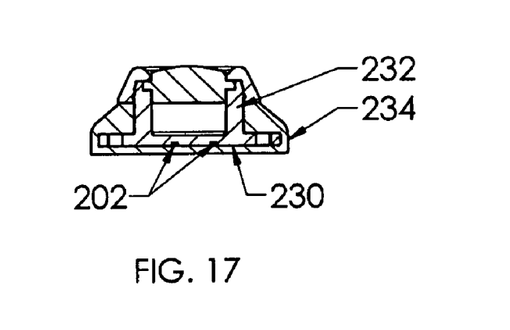
Figure 18:
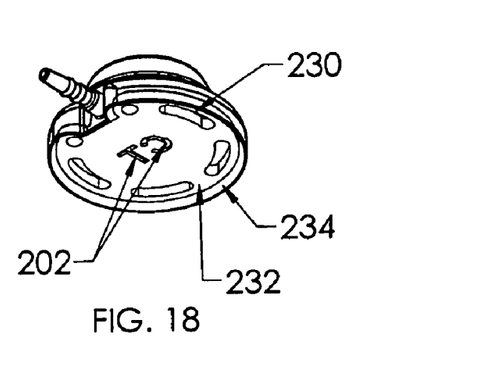

A second embodiment of X-ray discernable indicia is shown in FIG. 13, and is utilized in the port assemblies of FIGS. 14 to 18. In FIG. 13, the indicia comprise a set of discrete indicia elements of radiopaque material, such as being stamped from a sheet of titanium. Again, as is preferred, the indicia comprise the alphabetical letters "C" and "T" and are utilized together as a set. In FIGS. 14 and 15, the discrete elements are embedded into the thickness of the bottom wall 204 of housing base 206, so that they would not be visible from below (see FIG. 14) even though the silicone overmolded skirt 208 is transparent. However, the discrete letters 202 would clearly be visible on an X-ray very similarly to the port assembly shown in FIG. 11. Another manner of using discrete letters 202 is depicted in FIGS. 16 to 18, in which the letters 202 are insert molded along the bottom surface 230 of housing base 232 and recessed thereinto, preferably. With this variant, the radiopaque material may be titanium or may be, for example, silicone material having barium sulfate filler. In this case the mirror-image of "CT" would be visible from below as depicted in FIG. 18 after the silicone overmolding of skirt 234 about the exterior of housing base 232.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An implantable venous access port assembly, comprising:
    a needle-penetrable septum; and
    a housing securing the needle-penetrable septum, the housing comprising a housing base having a bottom wall and X-ray discernable indicia embedded in the bottom wall, the X-ray discernable indicia comprising one or more characters that visually indicate, under X-ray examination, a pressure property of the port assembly.

2. The assembly of claim 1, wherein the X-ray discernable indicia are a set of discrete elements.

3. The assembly of claim 2, wherein the discrete elements are of titanium.

4. The assembly of claim 2, wherein the discrete elements are of silicone with barium sulfate filler.

5. The assembly of claim 2, wherein the discrete elements are alphabetical letters.

6. The assembly of claim 2, wherein the bottom wall comprises an outwardly facing bottom surface comprising one or more shallow recesses, and wherein the discrete elements are affixed in the one or more shallow recesses of the bottom surface so that the discrete elements are visible to an unaided eye prior to implantation of the assembly.

7. The assembly of claim 2, wherein the discrete elements embedded in the bottom wall are embedded within a thickness of the bottom wall so that the discrete elements are not visible to an unaided eye prior to implantation of the assembly.

8. The assembly of claim 6, wherein the discrete elements are arranged in a first orientation visible under visual inspection of the port assembly, which first orientation is a mirror image of a second orientation of an image of the discrete elements perceived during X-ray examination.

9. The assembly of claim 6, wherein the housing comprises a skirt formed from radiotransparent material and molded around at least a portion of the housing base.

10. The assembly of claim 1, wherein the X-ray discernable indicia comprise a disc of radiopaque material, the disc comprising cutouts that indicate the pressure property of the port assembly.

11. The assembly of claim 10, wherein the cutouts are alphabetical letters.

12. The assembly of claim 10, wherein the disc is titanium.

13. The assembly of claim 10, wherein the bottom wall comprises an outwardly facing bottom surface comprising at least one shallow recess, and wherein the disc is affixed in the at least one shallow recess of the bottom surface so that the disc is visible to an unaided eye prior to implantation of the assembly.

14. The assembly of claim 10, wherein the disc embedded in the bottom wall is embedded within a thickness of the bottom wall so that the disc is not visible to an unaided eye prior to implantation of the assembly.

15. The assembly of claim 13, wherein the cutouts in the disc are arranged in a first orientation visible under visual inspection of the port assembly, which first orientation is a mirror image of a second orientation of an image of the cutouts perceived during X-ray examination.

16. The assembly of claim 13, wherein the housing comprises a skirt formed from radiotransparent material and molded around at least a portion of the housing base.

17. The assembly of claim 1, wherein the X-ray discernable indicia visually indicate, under X-ray examination, that the port assembly is rated to be used for power injection.

18. The assembly of claim 17, wherein the X-ray discernable indicia further visually indicate, under X-ray examination, that the port assembly is adapted to withstand high pressures used for injection of contrast fluid.

19. An implantable venous access port assembly, comprising:
   a housing comprising a housing base comprising a bottom wall and radiopaque indicia embedded in the bottom wall of the housing base, the radiopaque indicia comprising one or more characters indicating a pressure property of the port assembly under X-ray examination;
   a needle-penetrable septum; and
   a cap securing the needle-penetrable septum to the housing.

20. The port assembly of claim 19, wherein:
   the bottom wall of the housing base comprises a bottom surface comprising one or more shallow recesses, and
   the radiopaque indicia are affixed in the one or more shallow recesses of the bottom surface of the bottom wall, whereby the radiopaque indicia are visible by an unaided eye prior to implantation of the port assembly.

21. The port assembly of claim 20, wherein the radiopaque indicia comprise a metal disc affixed in the one or more shallow recesses of the bottom surface of the bottom wall, the metal disc comprising one or more cutouts indicating the pressure property of the port assembly.

22. The port assembly of claim 20, wherein the radiopaque indicia comprise one or more discrete metal elements separately affixed in the one or more shallow recesses of the bottom surface of the bottom wall.

23. The port assembly of claim 19, wherein the radiopaque indicia are embedded into a thickness of the bottom wall of the housing base, whereby the radiopaque indicia are not visible by an unaided eye prior to implantation of the port assembly.

24. The port assembly of claim 23, wherein the radiopaque indicia comprise a metal disc embedded into the thickness of the bottom wall of the housing base, the metal disc comprising one or more cutouts indicating the pressure property of the port assembly.

25. The port assembly of claim 23, wherein the radiopaque indicia comprise one or more discrete metal elements separately embedded into the thickness of the bottom wall of the housing base.

26. The port assembly of claim 19, wherein the radiopaque indicia indicate that the port assembly is rated to be used for power injection.

27. The port assembly of claim 26, wherein the radiopaque indicia indicate that the port assembly is adapted to withstand high pressures used for injection of contrast fluid.

28. An implantable venous access port assembly, comprising:
   a housing comprising a housing base and a skirt overmolded around at least a portion of the housing base, the housing base comprising a bottom wall and radiopaque indicia embedded in the bottom wall of the housing base, the radiopaque indicia comprising one or more characters indicating a pressure property of the port assembly under X-ray examination;
   a needle-penetrable septum; and
   a cap securing the needle-penetrable septum to the housing.

29. The port assembly of claim 28, wherein:
   the bottom wall of the housing base comprises a bottom surface comprising one or more shallow recesses, and
   the radiopaque indicia are affixed in the one or more shallow recesses of the bottom surface of the bottom wall.

30. The port assembly of claim 29, wherein the radiopaque indicia comprise a metal disc affixed in the one or more shallow recesses of the bottom surface of the bottom wall, the metal disc comprising one or more cutouts indicating the pressure property of the port assembly.

31. The port assembly of claim 30, wherein the overmolded skirt comprises a transparent material, whereby the metal disc comprising one or more cutouts is visible by an unaided eye prior to implantation of the port assembly.

32. The port assembly of claim 29, wherein the radiopaque indicia comprise one or more discrete metal elements separately affixed in the one or more shallow recesses of the bottom surface of the bottom wall.

33. The port assembly of claim 32, wherein the overmolded skirt comprises a transparent material, whereby the discrete metal elements are visible by an unaided eye prior to implantation of the port assembly.

34. The port assembly of claim 28, wherein the radiopaque indicia are embedded into a thickness of the bottom wall of the housing base, whereby the radiopaque indicia are not visible by an unaided eye prior to implantation of the port assembly.

35. The port assembly of claim 34, wherein the radiopaque indicia comprise a metal disc embedded into the thickness of the bottom wall of the housing base, the metal disc comprising one or more cutouts indicating the pressure property of the port assembly.

36. The port assembly of claim 34, wherein the radiopaque indicia comprise one or more discrete metal elements separately embedded into the thickness of the bottom wall of the housing base.

37. The port assembly of claim 28, wherein the radiopaque indicia indicate that the port assembly is rated to be used for power injection.

38. The port assembly of claim 37, wherein the radiopaque indicia indicate that the port assembly is adapted to withstand high pressures used for injection of contrast fluid.

39. The assembly of claim 1, wherein the one or more characters comprise one or more alphabetical letters.

40. The assembly of claim 39, wherein the one or more alphabetical letters comprise the letters "CT."

41. The port assembly of claim 19, wherein the one or more characters comprise one or more alphabetical letters.

42. The port assembly of claim 41, wherein the one or more alphabetical letters comprise the letters "CT."

43. The port assembly of claim 28, wherein the one or more characters comprise one or more alphabetical letters.

44. The port assembly of claim 43, wherein the one or more alphabetical letters comprise the letters "CT."

\* \* \* \* \*

UNITED STATES PATENT AND TRADEMARK OFFICE
CERTIFICATE OF CORRECTION

PATENT NO. : 8,021,324 B2
APPLICATION NO. : 12/175182
DATED : September 20, 2011
INVENTOR(S) : Bizup et al.

Page 1 of 1

It is certified that error appears in the above-identified patent and that said Letters Patent is hereby corrected as shown below:

On the Title Page

Item (75) Inventor is corrected to read:
-- Raymond Bizup, Feasterville (PA);
Kevin Sanford, Chalfont (PA);
Christopher Linden, Allentown (PA);
Kenneth M. Zinn, Westport (CT) --.

Signed and Sealed this
Twenty-second Day of December, 2020

Andrei Iancu
*Director of the United States Patent and Trademark Office*